United States Patent [19]

Gordon et al.

[11] Patent Number: 5,578,459
[45] Date of Patent: Nov. 26, 1996

[54] METHOD AND APPARATUS FOR COLLECTING A CELL SAMPLE FROM A LIQUID SPECIMEN

[75] Inventors: Julian Gordon, Lake Bluff; Donald I. Stimpson, Gurnee, both of Ill.; Wang-Ting Hsieh, Rockville, Md.

[73] Assignee: Abbott Laboratories, Abbott Park, Ill.

[21] Appl. No.: 158,233

[22] Filed: Nov. 24, 1993

[51] Int. Cl.$^6$ .............................. C12Q 1/02; C12M 1/12; B01D 29/05; B01D 39/18

[52] U.S. Cl. .................................. 135/29; 435/4; 435/6; 435/30; 435/287.2; 435/287.6; 435/288.2; 435/307.1; 436/177; 436/178; 210/321.6; 210/348; 210/455; 210/500.21; 210/650; 210/651

[58] Field of Search ................................ 435/4, 6, 30, 29, 435/287; 436/177, 178, 455, 456; 210/649, 650, 651, 653, 655, 348, 500.1, 500.21, 500.26, 500.29, 503, 505, 321.6; 128/897, 898

[56] References Cited

U.S. PATENT DOCUMENTS

| | | | |
|---|---|---|---|
| 3,888,629 | 6/1975 | Bagshawe | 436/541 |
| 4,690,757 | 9/1987 | Mathus et al. | 210/232 |
| 4,787,988 | 11/1988 | Bertoncini et al. | 210/808 |
| 4,891,134 | 1/1990 | Vcelka | 210/359 |
| 4,960,130 | 10/1990 | Guirguis | 128/760 |
| 5,003,988 | 4/1991 | Guirguis | 128/771 |
| 5,042,502 | 8/1991 | Guirguis | 128/771 |
| 5,190,666 | 3/1993 | Bisconte | 210/744 |
| 5,364,533 | 11/1994 | Ogura et al. | 210/645 |

OTHER PUBLICATIONS

Mennie, et al., "*Prenatal Screening for Cystic Fibrosis*", The Lancet, vol. 340, Jul. 25, 1992, pp. 214–215.

Seltzer, et al., "*Screening for Cystic Fibrosis: Feasibility of Molecular Genetic Analysis of Dried Blood Specimens*", Biochemical Medicine and Metabolic Biology, 46, pp. 105–109 (1991).

McCabe, "*Utility of PCR for DNA Analysis from Dried Blood Spots on Filter Paper Blotters*", PCR Methods and Applications, Review, pp. 99–106, 1991, by Cold Spring Harbor Laboratory Press.

Cyto–Shuttle, "*Cell Separation and Preparation Device*", Cancer Diagnostics, Inc., Lot No. 93 (no publication Date given).

Tsukahara et al. "Isolation of a γ Chromosomal DNA Sequence and Its Clinical Application" Abstract. Jpn J Human Genet. 35(4) 1990 331–340.

Fisher Scientific Catalog 1988 pp. 445 & 418.

Primary Examiner—David A. Redding
Assistant Examiner—Nancy T. Degen
Attorney, Agent, or Firm—Matthew R. Hooper

[57] ABSTRACT

A method and apparatus for collecting a cell sample from a liquid specimen utilizes a collection receptacle in which the specimen is deposited, with a filter media being place in communication with a discharge port in the collection receptacle and a transfer device for drawing specimen from the collection receptacle and through the filter for capturing the cellular component of the specimen on the filter media for defining a cell sample for analysis. The collection receptacle, filter media and carrier therefor and the transfer device may be supplied in kit form for use in a clinical environment. A hypobaric vessel may be used and the transfer device and this vessel may also serve as a disposal receptacle for the liquid specimen passed through the filter media.

24 Claims, 6 Drawing Sheets

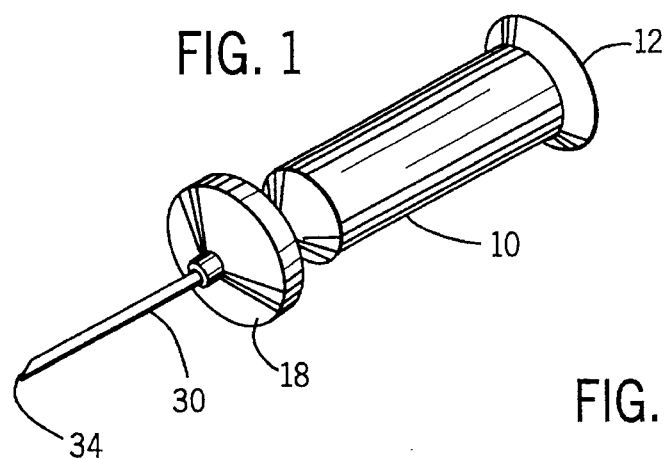
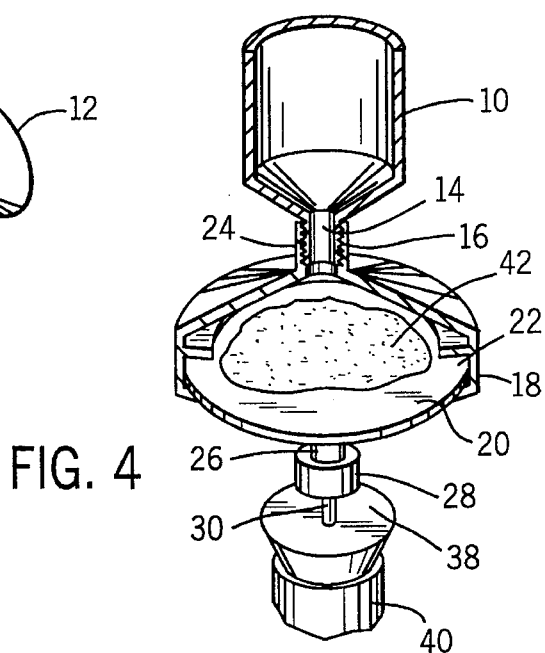
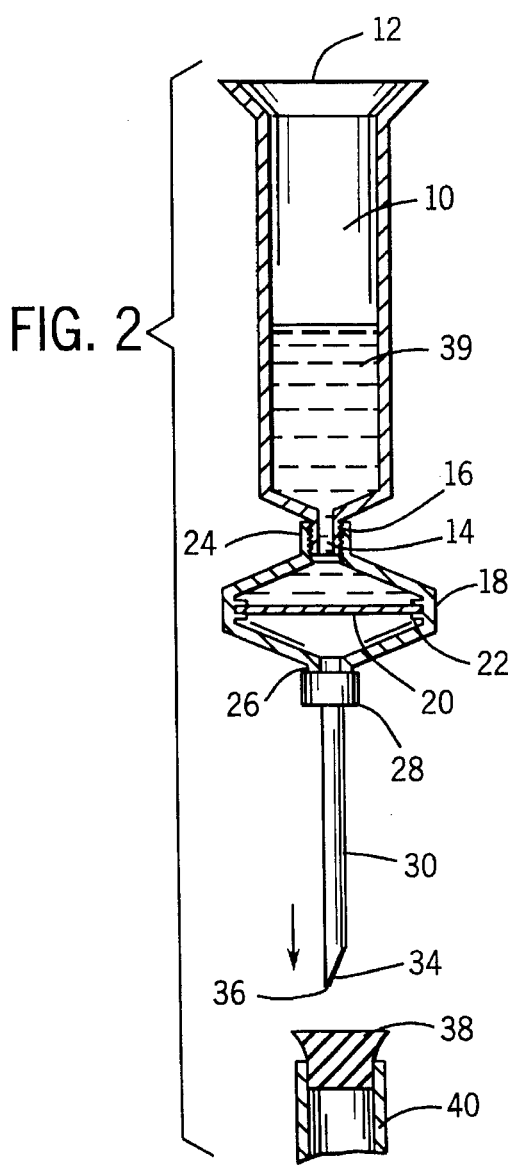
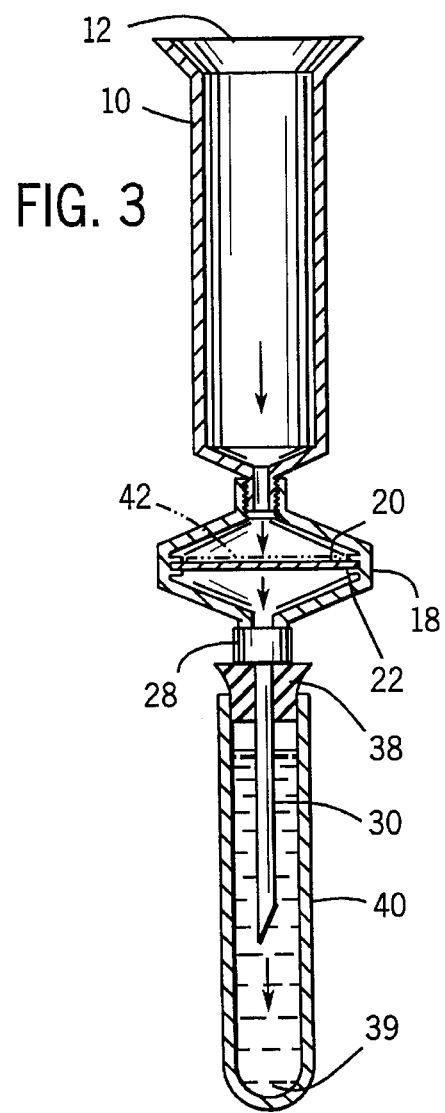

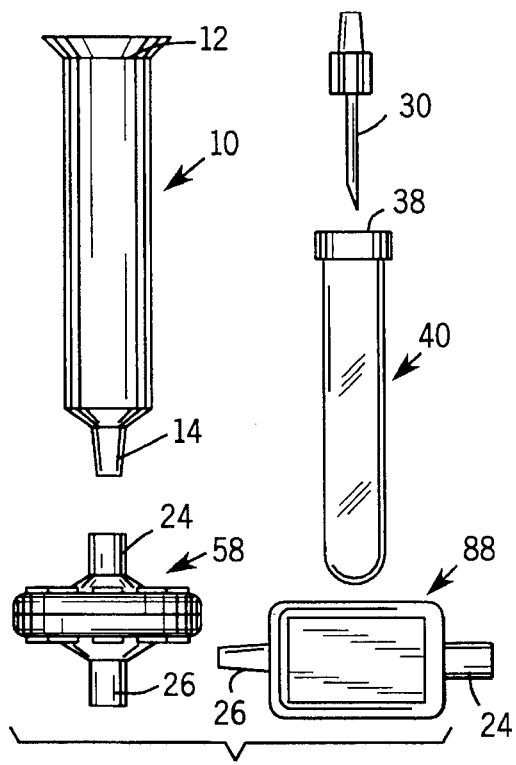
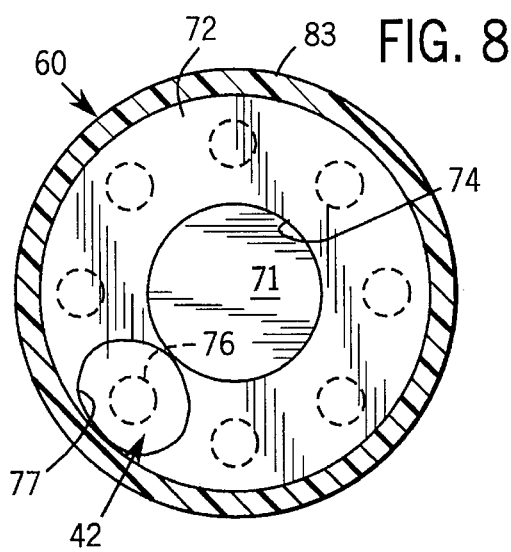
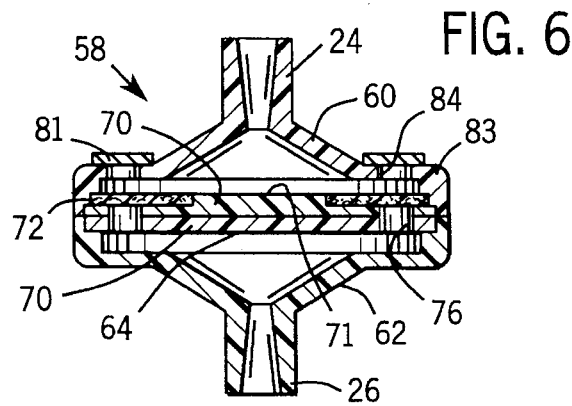
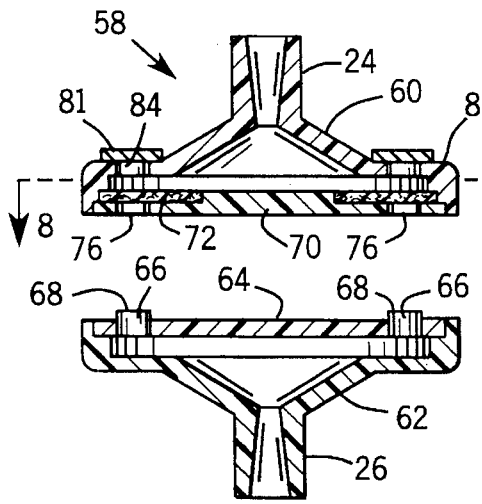
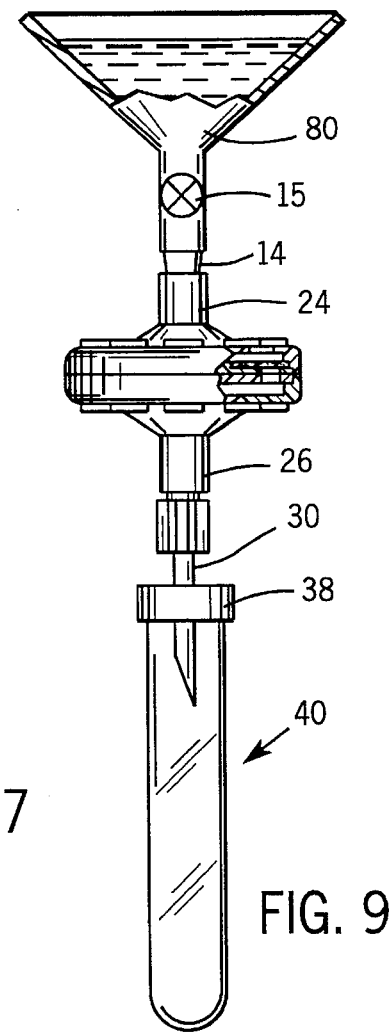

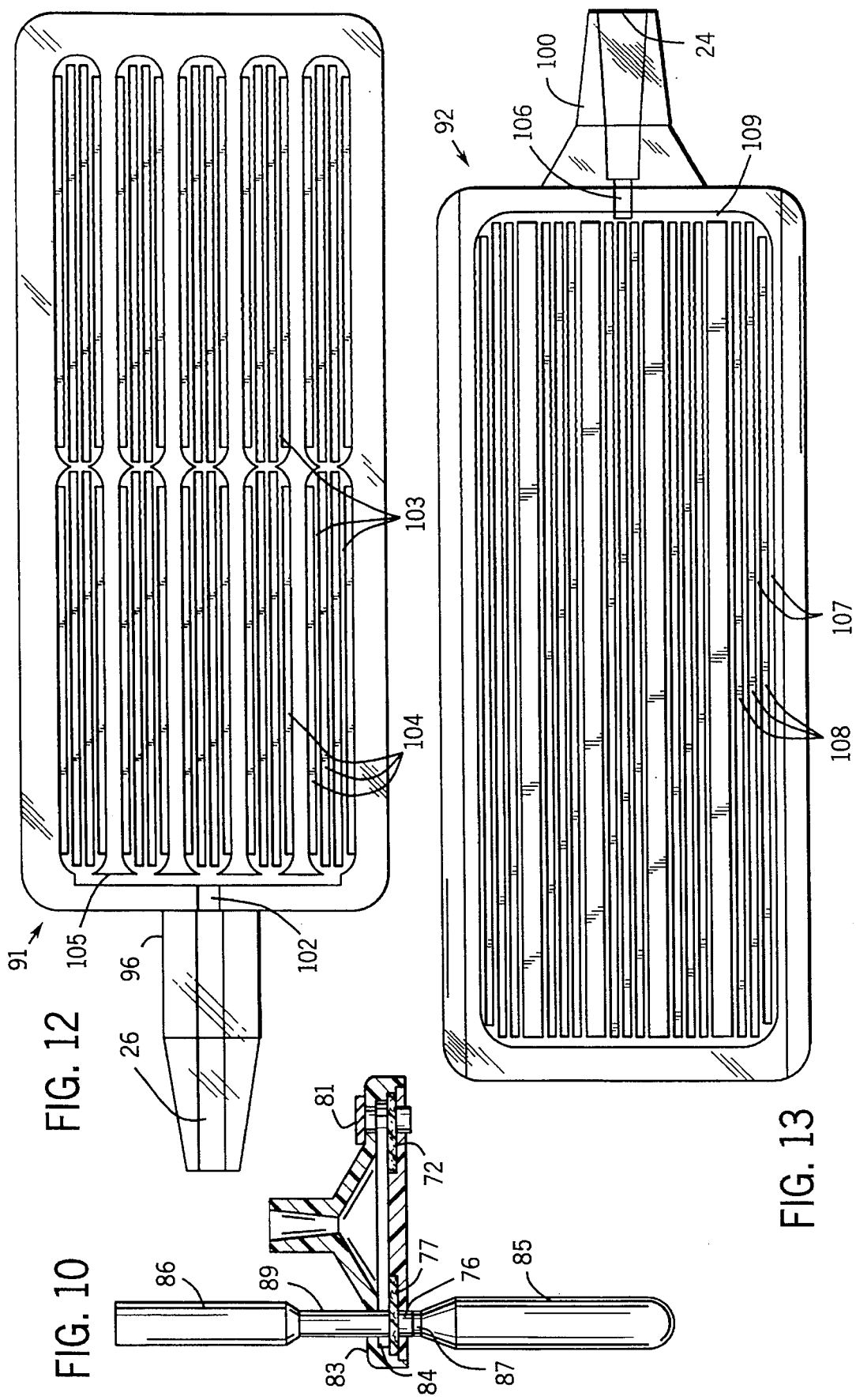

FIG. 15

SEQ ID. NO.

5. 5'-TATGCCTGGCACCATTAAAGAAAATATCATCTTTGGTGTTCCTATGATGAATATAGATACAGAAGCG.
1. 5'-F1-GGCACCATTAAAGAAAATATCA
2. 3'-CCGTGGTAATTTCTTTTATAG
3.                             GGTGTTTCCTATGATGAATATAG-BIO-3'
4.                             AGAAACCACAAAGGATACTACTTATATC-BIO-5'

FIG. 16

SEQ ID. NO.

10. CCAGGGCCTCACCACCAACTTCATCCACGTTCACCTTGCCCCACAGG
6. 5'adam-CCgAGGGCCTCACCACCAACTTCA
7. 3'-GGGTCCCGGAGTGGTTGAAG
8.                           CCACGTTCACCTTGCCCCACAGG-BIO-3'
9.                           AGGTGCAAGTGGAACGGGGTGTCC-BIO-5'

METHOD AND APPARATUS FOR COLLECTING A CELL SAMPLE FROM A LIQUID SPECIMEN

The invention is generally related to an apparatus for isolating cellular samples from liquid specimens such that the cells are available for subsequent analysis. More specifically, the invention is directed to a device for collecting high-volume liquid specimens, such as urine or mouthwashes, and separating the cellular components from the liquid component, the cellular component being used for analysis, including microscopy and DNA analysis.

BACKGROUND OF THE INVENTION

Collection of liquid specimens for laboratory analysis in order to detect the presence of specific diseases or conditions in a patient is well known. Typically, a liquid specimen or a swab is collected and, depending on the desired assay, the appropriate component of the specimen is extracted. In cases where the desired component is cellular or subcellular, the specimens are generally centrifuged to pellet the cells. The cell pellets are optionally lysed to release a subcellular component. Alternatively, lysis may occur prior to centrifugation and the pelleted debris can be analyzed. Because centrifugation equipment is not readily portable, specimen collection, especially high-volume liquid specimen collections, have generally been limited to the clinical or laboratory setting. While swabs have been transported for years, the collection process generally requires trained technicians to assure the collection of a useful specimen and careful storage and transport of resuspended cells from the swab.

More recently, mouthwash specimens have been introduced as a method of collecting patient cell specimens for analysis. Typically, a patient is given an oral rinse or mouthwash which is expectorated into a collection container upon completion of the rinse step. The resulting mouthwash specimen contains saliva and sloughed buccal cells mixed in with the expectorated rinse. Such a mouthwash specimen can be analyzed to determine its various components or certain patient attributes.

For example, as reported in The Lancet, Vol. 340, Jul. 25, 1992, pp 214–216, a method of collecting mouthwash specimens to collect patient cells for cystic fibrosis screening has been studied in the United Kingdom. Cellmark Diagnostics has also developed a method for extraction of DNA from mouthwash specimens as part of its CF Mutation Analysis System. In the Cellmark process, once the mouthwash specimen is collected, it is centrifuged and the desired components are extracted from the pelleted cells.

The centrifugation step is normally done at the collection site. In order to perform the collection and analysis using this system, the collection of the specimen must be at a site where equipment is available for centrifugation and extraction. In addition, only a small percentage of the total specimen is required for tests. This means that since the entire specimen must be kept viable, the entire specimen must be stored until the extraction step is completed. In a typical example, only one percent of the specimen is required for an analysis. This means 99% of the storage specimen is ultimately discarded. By maintaining such a large specimen, the costs of transportation, storage and disposal of the specimen becomes critical.

While mouthwash collection has been found to be an efficient and desirable, non-invasive method of collecting cell specimens from a human patient, the transportation, storage and disposal problems have minimized its widespread acceptability. In addition, the fact that the primary cell collection steps must be performed at a central location further diminish the value of this method of collection.

In order to analyze mouthwash specimens properly, the specimens must be collected in fluid form in a sterile container, sealed and transported to the central centrifugation and extraction site. This is also true of most other collected liquid specimens of bodily fluids.

Therefore, the advantages of specimen collection are often outweighed by the disadvantages of the cumbersome, inconvenient and costly steps required in the storage preservation and transportation of the specimen to an analysis site. In order for the liquid specimen techniques to gain widespread acceptance, a need must be met to minimize the difficulty in collecting, storing and transferring the specimens obtainable from the liquid solution.

For example, U.S. Pat. No. 3,888,629, entitled: Performance of Chemical or Biological Reactions within Absorbent Matrix Pad, issued to K. D. Bagshawe on Jun. 10, 1975 shows a system for drawing a liquid specimen through a discrete matrix pad for analysis of an antigenic component. It does not, however, deal with the collection of the original specimen or with the isolation of cells for analysis. This is also true with the device shown and described in U.S. Pat. No. 4,891,134, entitled: Specimen Filtration Device, issued to J. Vcelka on Jan. 2, 1990. In both of these documents the cells are lysed to release the antigenic component of interest prior to application to the matrix filter.

While numerous examples are available for introducing a specimen to a test medium such as a matrix pad or the like, the clinical use of such systems has generally been limited because of the requirement for the entire liquid test specimen to be transported in a liquid state from the collection site to the analysis facility, thereby requiring sealed, sterile containers and shipping parcels which must be handled with great care. This is true whether the specimen is generated using invasive techniques (such as the collection of blood specimens) or in an non-invasive manner (such as urine or mouthwash specimens). Therefore, there remains a need to improve the clinical environment for the collection and transportation of liquid specimens.

The so-called "Guthrie Spot" is universally used for screening neonatal whole blood for a variety of products of errors of metabolism {R. Guthrie, Organization of a regional newborn screening laboratory, in *Neonatal screening for inborn error of metabolism* (ed. H. Bickel, R. Guthrie and G Hammersen), pp 259–270, Springer Verlag, Berlin 1980}. The dried blood spots are of great utility because they facilitate the ability to ship, archive and perform multiple analyses on the same sample. More recently, the utility of such dried blood spots has been extended to tests involving DNA amplification and analysis (McCabe ERB. 1991. Utility of PCR for DNA Analysis from Dried Blood Spots on Filter Paper Blotters, in PCR *Methods and Applications*, Volume 1:pp 99–106). Application of the technique is limited, however, and has only been applied to analysis of blood samples. Moreover, it does not involve any separation of cells from a liquid component. Both cells and serum remain on the filter. The present invention, as will be seen, extends the utility and obviates these disadvantages of the Guthrie Spot.

SUMMARY OF THE INVENTION

The subject invention is directed to a method and apparatus for expediting the collection and transfer of cellular components of bodily fluids collected as a liquid specimen. The invention is particularly useful in the isolation of cellular components of high-volume liquid specimens, especially those collected by way of non-invasive processes, such as by way of example, buccal cells which may be collected from a mouthwash specimen, or pathogen cells which may be found in urine. However, it will be understood that the invention can also be utilized for collection and analysis of other liquid specimens collected through invasive techniques, such as blood or CSF specimens and the like.

Thus, in a first aspect, the invention relates to a cell collection apparatus for collecting, archiving and transporting a cell sample generated from a liquid specimen, comprising:

a liquid specimen collection container having an open end for receiving a liquid specimen and a discharge port through which said liquid specimen can leave the collection container;

a filter container having an inlet port adapted for sealably engaging the discharge port of said collection container, an outlet port through which said liquid specimen can leave the filter container and a filter media supported in the container between said inlet and outlet ports, whereby liquid specimen entering said filter container via the inlet port passes through said filter media before leaving via said outlet port, said filter media being adapted for receiving and capturing a cellular component of the liquid specimen for defining a cell sample for analysis; and means for creating and applying a reduced pressure to the outlet port of said filter container, thereby drawing the liquid specimen through the filter media.

Preferably the cell collection apparatus further comprises a discharge vessel for receiving the liquid specimen passing through the filter media and the outlet port of the filter container; and more preferably the means for creating and applying reduced pressure is a hypobaric vessel adapted to be coupled in sealed engagement with the outlet port of the filter container. The hypobaric vessel can thus simultaneously serve as the means for applying pressure and the discharge vessel. A Vacutainer™ vessel has been found convenient and suitable for a combined discharge vessel and means for applying reduced pressure in accordance with the present invention.

The cell collection apparatus may also include a hollow-bore needle in communication with said filter container outlet port, said needle being adapted for piercing a rupturable seal on said hypobaric vessel, thereby applying a reduced pressure to the outlet port.

Preferably, the filter media is a discrete element, all or part of which is removable from said filter container. It may be made of a material selected from the group consisting of glass fiber, paper and cellulose esters. To facilitate removal of the filter, the filter container housing may comprise a pair of mated members. In such case, the one member may include a filter support means for supporting the filter media. The filter housing preferably also includes channeling means for distributing liquid specimen to discrete areas of the filter media.

In another aspect, the invention relates to methods of collecting cellular samples from liquid specimens, the method comprising the steps of:

depositing a liquid specimen suspected of having a cellular component into an open end of a collection receptacle having a discharge port;

placing the discharge port in fluid communication with a filter media by means of a sealed passage therebetween, the filter media having a pore size sufficiently small to retain desired suspected cells from the specimen, the; and applying a pressure differential across the filter and extending to the collected specimen by means of the sealed passage to force the liquid specimen through the discharge port of the collection receptacle and through the filter media, thereby capturing on the filter media any cellular component of the liquid specimen.

The pressure differential may be created by placing the outlet port of the filter container under a relative vacuum, such as is accomplished by placing a closed hypobaric chamber in fluid communication with said outlet port. Typically, the hypobaric chamber includes a penetrable closure element, and is selectively placed in fluid communication with said outlet port by mounting a hollow bore needle to said filter container such that the bore of the needle is in fluid communication with the outlet port, and puncturing the closure element with the needle, thereby placing the filter container under hypobaric pressure.

Following collection of cells in the above manner, at least some of the filter media may be removed from the filter container and the sample dried on the filter media. Removal can be by opening of mated halves of the filter container housing, or by punching portions of the filter media to the exterior of the housing. The cell sample can then be sectioned, stored, transported and/or analyzed according to the wishes of the clinician.

While the cell sample can be analyzed for any number of consitutents, by any number of known analytical techniques, a preferred constituent for analysis is a segment of nucleic acid, preferably the RNA or DNA from the cells. Such nucleic acid may be analyzed in situ or by amplification, such as by PCR or LCR.

It is presently preferred that the liquid specimen is a high-volume specimen, such as a mouthwash specimen.

In a further aspect, the invention relates to kits containing the components of the apparatus for practicing the above methods.

The subject invention permits the rapid collection of cells on a filter media in a manner that can be performed at any site without special equipment or special training, producing a very portable and transportable filter paper specimen which can be dried and archived for one or more subsequent analyses. The cell collection method and apparatus of the subject invention has an unexpected desired result in that the collection of buccal cells quickly after the mouthwash specimen has been produced has provided unusually high and consistent yield of cells in each collected sample.

The invention provides a desirable method and apparatus for use in any application where liquid specimens are collected for analysis of the cellular component thereof, and has proven to be particularly useful in DNA amplification technology such as for the investigation of genetic defects, carrier status for genetic defects, as well as forensic, identity, military or paternity applications.

The invention is readily adapted to be supplied to clinical technicians in kit form with an integrated collection receptacle, filter media pack and hypobaric vessel. The method of specimen collection and sample capture is quickly mastered without specialized training and consistently yields excellent samples for analysis. The components of the kit are inexpensive and their use is consistent with widely known, proven laboratory techniques.

It is, therefore, an object and feature of the subject invention to provide specimen collection apparatus for collecting a cell rich sample for archiving, transporting and subsequent analysis.

It is another object and feature of the subject invention to provide a specimen collection device for collecting human cells on a filter media by drawing the specimen through the filter.

It is also an object and feature of the subject invention to provide a sample collection kit utilizing equipment of a nature widely used and accepted in a clinical environment.

It is a further object and feature of the subject invention to provide a method for collecting cell samples on a filter media by drawing a liquid sample through the filter for trapping the cellular components of the sample in the media.

Other objects and features of the invention will be readily apparent from the accompanying drawings and detailed description of the preferred embodiment.

BRIEF DESCRIPTION OF THE DRAWING FIGURES

FIG. 1 is a perspective view of a specimen collection apparatus of the subject invention, particularly well suited for use in connection with mouthwash specimens.

FIG. 2 is a longitudinal cross-section of the specimen collection apparatus shown in FIG. 1.

FIG. 3 is a view looking in the same direction as FIG. 2, showing the collection apparatus after the specimen has been drawn through the filter container for collecting on the filter media a sample containing the cellular component of the specimen.

FIG. 4 is an enlarged, fragmentary view diagrammatically illustrating the capture of the cellular component of the liquid specimen on the filter media.

FIG. 5 illustrates the components of a typical kit embodying the present invention.

FIG. 6 is a cross section of another embodiment of the filter container of the invention.

FIG. 7 is a cross-section like FIG. 6, showing the container separated into its mated halves to provide access to the filter media.

FIG. 8 is a cross section taken generally along line 8—8 of FIG. 7.

FIG. 9 is similar to FIG. 3, utilizing the filter container of FIGS. 6, 7 and 8.

FIG. 10 illustrates a method for removing collected cells from the filter media into an assay tube.

FIG. 12 is a plan view of the device of FIG. 11, showing the underside of the top half.

FIG. 13 is a plan view of the device of FIG. 11, showing the topside of the bottom half.

FIGS. 15 and 16 show how the specific LCR probes used in examples 4 and 5, respectively, align on their respective targets.

Figure 17:
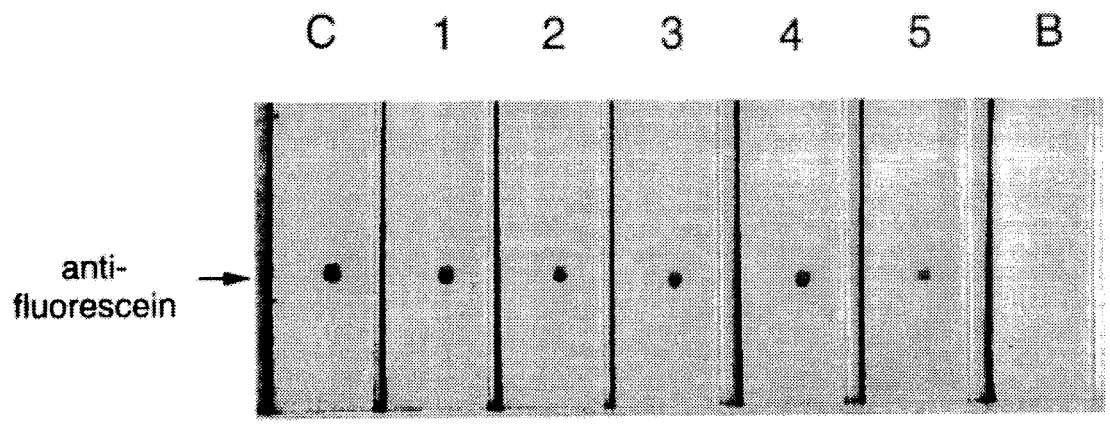
Figure 18:
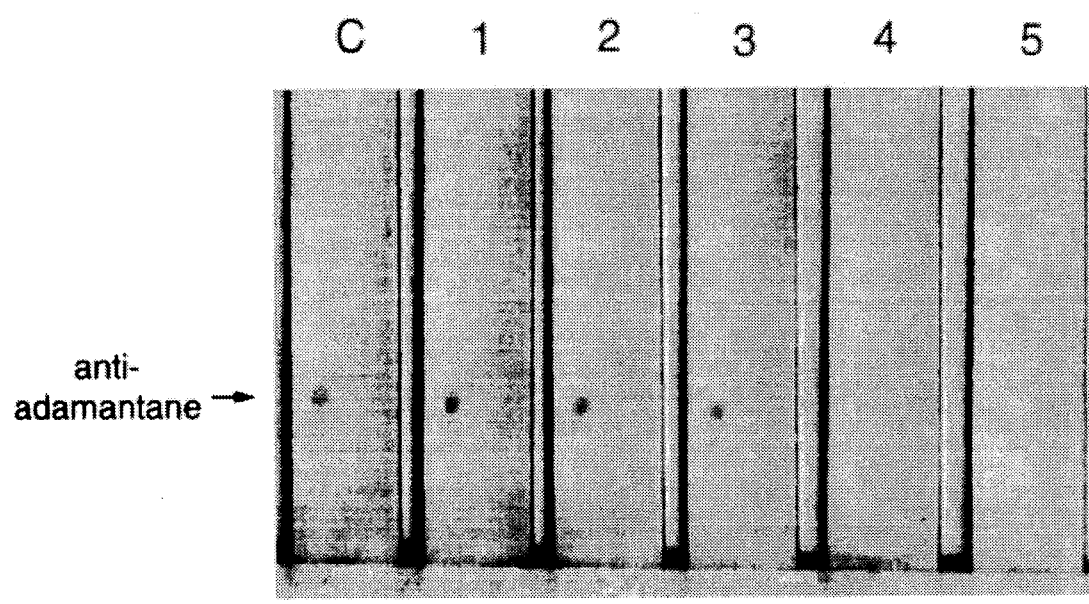

FIGS. 17 and 18 are photographs of strips on which DNA was tested after cells were collected in accordance with the invention, and are described in more detail in examples 4 and 5, respectively.

DETAILED DESCRIPTION OF THE INVENTION

The invention will now be described in detail, including an explanation of the methods and theory as well as several varied embodiments thereof and working examples.

Part I: General Description

The collection apparatus of the invention is particularly well suited for collecting and archiving cells extracted from a liquid specimen for analysis. In the present invention, a liquid "specimen" is distinguished from a "sample" in that a "specimen" is the raw material collected from the patient, while a "sample" denotes a specimen that has been processed in some way; for example by concentrating sample cells by removal of the bulk of the liquid portion of the original specimen. Liquid specimens may be obtained by invasive techniques, as in the case of blood or cerebrospinal fluid (CSF); or they may be non-invasively obtained, as with urine, or rinses of various body parts or cavities, including but not limited to vaginal douches, mouthwashes, and the like. A "rinse" or "lavage" refers to the use of a volume of liquid to wash over or through a body part or cavity, resulting in a mixture of liquid and cells from the body part or cavity.

A liquid specimen is considered a "high-volume" specimen when the amount of desired sample component is small relative to the quantity of liquid present. For example, urine and and mouthwashes are considered "high-volume" specimens since the expected cellular content (typically bacterial and buccal cells, respectively) is small relative to the volume of liquid obtained as the specimen. High volume specimens should be distinguished from specimens such as culture swabs or centrifuge pellets which are often resuspended in a limited amount of a diluent solution.

Specimens may be collected from almost any source, including without limitation, humans, animals, foods, the environment and the like. These liquid specimens are collected in a collection receptacle and drawn therefrom through a filter media which is selected to extract a cellular component sample from the specimen. The cell specimen on the filter media may then be analyzed. The invention is designed to incorporate methodology familiar to clinical technicians and relies on the used of a pressure across the filter media to draw the specimen therethrough.

In general, the systems of the present invention comprise three components: a collection receptacle, a filter media (generally enclosed in a housing) and a fluid collector tube.

A first embodiment of the collection apparatus is shown in FIGS. 1–4. The collection apparatus there shown is well-suited for use with a collection receptacle 10 having a slightly enlarged mouth 12 through which a high-volume specimen such as an oral rinse or the like may be deposited. It will be readily understood that other collection receptacles could be substituted for the receptacle 10, whereby the collection apparatus of the subject invention could be used for collecting and archiving other liquid specimens.

As best shown in FIGS. 1 and 2, the collection apparatus of the subject invention comprises a filter container 18 for supporting a filter media 20 between an inlet port 24 and an outlet port 26. The inlet port 24 is adapted to communicate with the discharge port 14 of the collection receptacle, whereby a fluid specimen collected in the collection receptacle 10 may be discharged into the inlet port 24 and transferred through the filter 20 to the outlet port 26. As the fluid specimen flows through the filter container 18, the cellular component of the specimen is captured and collected on the filter media to provide a cell sample. The cell sample captured on the filter 20 may then be archived and/or transported for later analysis. It is an important feature of the invention that the filter 20 may be dried and stored for easy transport to a clinical analysis facility.

In experimental tests, it has been found that any of a variety of commercially available filter elements produce suitable results in capturing high yield cell samples from a collected liquid specimen. The filter media will have a depth and pore size (or particle retention size) which is dictated primarily by the size of the cellular component to be extracted and examined. It may be desirable to utilize composite filter media of different ratings, particularly to assure efficient collection of cells from a specimen that may contain mucous material. In the preferred embodiment of the invention, the filter is a bonded glass fiber depth filter such as the type commonly used as prefilters.

The physical properties of selected filter media are presented in the following table:

negative pressure or vacuum applied to the underside of the filter 20. This draws the liquid through the filter media as the cellular components of the specimen are collected on the filter.

According to a most preferred configuration, the disposal vessel 40 also provides the negative pressure on the underside of the filter. This can be easily accomplished through the use of an evacuated vessel or tube which, upon connection to the outlet port 26, draws the liquid through the filter and into the disposal tube 40. Such an evacuated vessel need not represent a complete vacuum but need only represent a sufficiently low pressure to permit the drawing of a sufficient volume of liquid through the filter media. Thus, such a vessel is referred to herein as a "hypobaric" or "subatmospheric pressure" vessel or chamber. A suitable example of a hypobaric vessel is the evacuated tube known as Vacutainer™, produced and sold by Becton-Dickinson, Rutherford, N.J.

TABLE

| Source | Membrane | Particle retention (μ) | Filtration rate* | Thickness (mm) |
|---|---|---|---|---|
| Millipore | AP15 | 0.2–0.6† | 5.8 | 0.49 mm |
| Millipore | AP25 | 0.8–8† | 3.2 | 0.92 |
| Millipore | AP40 | none given | 3.9 | 0.41 |
| Whatman | GF/A | 1.6 | 13 | 0.25 |
| Whatman | GF/B | 1.0 | 5.5 | 0.68 |
| Whatman | CF/C | 1.2 | 10.5 | 0.2 |
| Whatman | GF/D | 2.7 | 16.5 | 0.68 |
| Whatman | GF/F | 0.7 | 6.0 | 0.42 |
| Fisher | G8 | 2.5 | 0.5 | 0.69 |
| Fisher | G2 | 2 | 4.8 | 0.66 |
| Fisher | G6 | 1.5 | 1.6 | 0.32 |
| Fisher | G4 | 1.2 | 3.2 | 0.28 |
| Gelman | A/E Binder free | 1 | 3.1 | 0.45 |
| Gelman | Extra thick | 1 | 7.4 | 1.3 |
| Gelman | Metrigard | 0.5 | 19.5 | 0.43 |
| Poretics | Mixed ester cellulose | 5 | 3.4 | 0.175 |
| Poretics | Mixed ester cellulose | 3 | 4.5 | 0.175 |
| Poretics | Mixed ester cellulose | 1.2 | 6.0 | 0.175 |
| Poretics | Mixed ester cellulose | 0.8 | 8.4 | 0.175 |
| Poretics | Mixed ester cellulose | 0.7 | 11 | 0.15 |
| Poretics | Mixed ester cellulose | 0.65 | 11.5 | 0.15 |
| Poretics | Mixed ester cellulose | 0.45 | 39 | 0.15 |
| Poretics | Mixed ester cellulose | 0.3 | 71 | 0.15 |
| Poretics | Mixed ester cellulose | 0.22 | 87 | 0.125 |

*The manufacturers' specifications have been reduced to a common unit, namely time in sec for 100 ml to pass through a 2.2 in diam filter at 1.9 psi.
†Although no retention size was given, the manufacturer indicates that AP15 and AP25 are "good" as prefilters for filters having the retention range listed.

It can be seen from this table that the composition of the filter media 20 is not crucial; it may be paper, glass fiber, esters of cellulose or other composition. What is more important is that a filter media is selected that has a retention size compatible with the approximate size of the cells to be filtered. Selecting the largest such suitable media will enable the fastest flow rates. From the above table, it is possible for the person skilled in the art to select a suitable filter media based on these criteria, provided the approximate size of the cells to be filtered is known or can be determined.

Liquid specimens in the collection receptacle 10 are forced through the discharge port 14, the inlet port 24 and the filter media 20 before exiting the filter container 18 via the outlet port 26. Preferably the outlet port is connected to a disposal container 40 which collects the filtrate which is to be discarded. The driving force for this movement of liquid is a pressure differential across the filter media. Although the pressure differential may be created by positive pressure from above the filter 20, the preferred method utilizes a Preferably the hypobaric vessel includes a closure 38 such as a stopper or septum that can selectively be opened to the outlet port 24 of the filter container 18. As an alternative, a valving means could be used as a selective closure.

Ideally the connections between the collection receptacle discharge port and the filter container inlet port, and between the filter container outlet and the means for generating a pressure differential across the filter are "sealing engagements", by which is meant that the connection is essentially air-tight. It is important that the connections be essentially airtight for proper operation. The reduced pressure at the filter container outlet will draw liquid specimen through the filter media when the driving force, atmospheric pressure, is applied at the open end of the collection receptacle on top of the fluid. If leaks or poor seals permit atmospheric pressure to enter the system below the head of liquid specimen, the flow and filtration will be inefficient. This caveat applies to filter container housings that are formed as two mated halves as well as to the connections between component parts of the apparatus.

The physical principles that govern the collection device can be understood in terms of the theory that describes pressure driven filtration. Application of a pressure gradient P to a filter medium results in a flow of liquid volume V per unit time t. The equation that relates these variables is:

$$dV/dt = KP/u$$

where u is the liquid viscosity and K is the flow coefficient. In a system where the pressure gradient is provided by an evacuated chamber, P may be presumed to equal one atmosphere. The flow coefficient K is equal to the inverse of the resistance, R, to liquid flow through the membrane; K=1/R.

In addition, the volume of specimen fluid passing through the collection membrane contains cells. As the cells are trapped in the membrane the resistance to fluid flow, R, increases. To simplify the model we assume that the resistance to fluid flow changes in a linear fashion with membrane loading, or K=Km (1−CV/W) where Km is the initial membrane coefficient, C is the number of cells per unit volume V, and W is the maximum number of cells the membrane can hold. In this approximation the flow coefficient starts off at Km and decreases to zero when the volume of liquid passing through the membrane contains the maximum number of cells that the membrane can hold. The phenomenon of increasing membrane resistance as a result of the filtration process is generally termed "membrane fouling". More accurate descriptions of membrane fouling can be derived, however, they will not substantially change the qualitative description of the sample collection device of the invention.

Another feature of the present system is the use of a finite volume hypobaric vessel to provide the driving force for filtration of the specimen. As the liquid specimen is pulled into the hypobaric vessel the pressure will change as predicted by the equation PV=nRT where P is the pressure, V is the vessel volume, n is the concentration of gas, R is the gas constant the T is the temperature. The equation that describes filling of a hypobaric vessel or Vacutainer™ tube is:

$$P_i = \frac{P_O}{V_O - V}$$

where $P_o$ is the initial pressure inside the vessel of volume $V_o$ and $P_i$ is the pressure inside the vessel after volume V of specimen has been filtered. While it is not possible to create a perfect vacuum, every effort is made to create the best vacuum possible. For our purposes we will assume that $P_o=0$, i.e., we have a perfect vacuum inside the hypobaric vessel so that $P_i$ remains constant and equal to zero during sample collection. For this reason, filtration in the specimen collection device can be assumed to be carried out under the constant pressure of 1 atmosphere.

The flow of liquid specimen is therefore described by the equation:

$$dV/dt = \frac{Km(1 - CV/W) \cdot P}{u}$$

whose solution is:

$$V = \frac{W}{C(1 - e^{-t \cdot Km \cdot (P/u) \cdot (C/w)})} = \frac{W}{C(1 - e^{-t/S})}$$

where S is a rate constant defined as $$S = \frac{u \cdot W}{km \cdot P \cdot C}.$$

Empirically, flow for a mouthwash specimen is observed to be initially very rapid followed by a sharp drop in flow rate in about 30 seconds after about 10 cc of liquid has been filtered. The long term behavior of the system is characterized by very slow flow or, for practical purposes, flow stops. Thus, the observed behavior is in complete qualitative agreement with our simple exponential model. In addition, an empirical estimate of S may be obtained for a typical sample because it is generally accepted that long term behavior of an exponentially relaxing system is obtained by 6×S; thus S=30/6=5 seconds.

From this simple model we can predict that the apparatus will collect approximately the same number of cells independent of the starting cell concentration. For example, if one sample filters 10 cc of specimen and stops in 30 seconds, a specimen with twice the cell concentration will filter 5 cc in 15 seconds and both collected samples will contain the same number of cells.

If a specimen does not contain a sufficient concentration of cells, the maximum loading of the membrane W will not be achieved due to the finite capacity of the hypobaric vessel. However, this situation can be avoided by providing a volume mark on the disposal vessel and discarding any specimen and associated sample that resulted in a filtered volume greater than this value.

Of course in reality a perfect vacuum is not necessary or attainable. Typically, the vacuum is calibrated to inhale a defined volume. This means that $P_o$ does not actually equal zero, and that the driving pressure gradient is not constant and approaches unity as the disposal tube acquires its defined volume of liquid. This fact complicates the model equations somewhat, but does not qualitatively affect the conclusions.

Once the cellular component of the specimen is deposited on the filter medium, the cell sample can be prepared for subsequent analysis. Both the preparation steps and subsequent analysis steps may vary greatly depending on the situation. For example, the filter media is typically removed from the filter container 18 and the cell sample is generally dried onto the filter. After drying, the filter and its cell sample may be stored and/or transported to an analysis site, either local or remote, for subsequent analysis. The filter media may be sectioned into aliquots for a plurality of tests where desired.

Typical analyses performed on such cell samples include, without limitation, DNA analysis, immunological analysis, direct staining for observation by microscopic analysis. In some instances, the cells will be removed from the filter by resolubilization in a buffer or diluent. The cells may optionally be treated with detergents, such as when cell lysis is desired to release internal molecules or structures for analysis. In cases of stubborn cells, such as plant cells and Mycobacterium, the cells may require breakdown by physical, mechanical or ultrasonic means. Typical DNA analyses include: standard hybridizations such as dot blot and the like, with or without prior amplification of signal or target. Signal amplification schemes useful with DNA analysis include multimer or chain branched labels, enzyme labels and the like. Target amplification schemes include LCR and PCR. Specific examples of analysis of the DNA molecules of cells collected in accordance with the invention are provided in Part III, infra.

Alternatively, the cells may be treated with permeability enhancers, pore-forming agents, or other similar fixative agents, such as when in-situ hybridization is the contemplated method for analysis. Such analysis methods are known in the art, as exemplified by, e.g. U.S. Pat. No. 5,225,326, issued Jul. 6, 1993 to Bresser, et al. In short, it should be clear that virtually any analysis method may be employed on cells collected according to the invention.

An unique and surprising feature of the invention is the ability to microscopically observe cells directly on most filter media. The only limitation appears to be the intensity of light and, if sufficient, cells can be observed even on dried filter media. Visualization is enhanced, however, when the filter element is wetted with water prior to observation.

Part II: Various Specific Embodiments

The general concepts described above are further illustrated in three specific embodiments described here.

In the embodiment shown in FIGS. 1–4, the components are readily available and familiar parts. For example, it has been found that a 20 ml to 50 ml syringe barrel, with the needle removed, is a suitable collection receptacle 10, although other collection receptacles may be readily adapted to the method and apparatus of the invention in the manner well known to those skilled in the art. Ideally, the design and configuration of the collection receptacle 10 is governed by the volume and source of the liquid specimen which it must collect. For instance the open mouth 12 can be specially configured to facilitate close contact with the source of the specimen so as to minimize any spillage or loss of specimen volume.

The discharge port 14 of the syringe barrel receptacle 10 is a cylindrical, protruding male element having external threads at 16. The threads are designed to sealingly engage the inlet port 24 of the filter container 18. The discharge port 14 may optionally include a removable seal or a stop cock or valve (illustrated at 15 in FIG. 9 in connection with another embodiment) so that the filter container 18 may be connected to the collection receptacle after collection of the liquid specimen without leakage of the specimen. Alternatively, the valve when utilized may be placed directly on the filter container.

In the preferred embodiments, a filter container 18 is adapted for housing and enveloping a filter media such as filter paper 20. Where desired, the filter paper 20 can be supported or retained in a filter support such as the peripheral or annular channel 22 defined by a pair of annular flanges provided in the inner sidewall of the container 18. As noted, the inlet port 24 on the container 18 is a female, internally threaded receptacle adapted to be threadably secured to the discharge port 14 of the receptacle 10. The means for connecting the receptacle 10 to the filter container 18 is not critical, as long as the connection does not leak. The threaded connection is used simply as a matter of choice, although other known mechanisms for sealing (e.g., Luer-Lok™ or bayonet type) are also within the scope of the invention.

The container 18 includes an outlet port 26 through which the filtered liquid specimen exits the filter container. In this embodiment, the outlet port is an externally threaded cylindrical extension adapted for receiving the base 28 of a typical hypodermic needle 30. The base 28 of the needle 30 is typically internally threaded for sealing engagement with the port 26. As is also typical, the hypodermic needle 30 has a hollow bore 32, and is cut on a bias as shown at 34 to form a sharp point at 36. In order to assure sterility and to seal the needle, a thin, frangible membrane is typically provided over the opening at the end to close the tube channel 30.

The filter container 18 is preferably made of at least two sections adapted to be mated together such that the sections may be separated to remove the filter media 20 without destruction.

In this first embodiment, a 16 gauge hypodermic needle is attached to the outlet port 26 of the container, for use in combination with a 14 ml. Vacutainer™ hypobaric chamber which also serves as a disposal vessel 40 for the spent specimen. In the embodiment shown, the vessel 40 is placed in sealed communication with the outlet port 26 of the filter container 18 by inserting the sharp tip 36 of the needle 30 into and through the sealing cap or stopper 38 of the vessel 40, as shown in FIGS. 2 and 3. When the needle is in sealed communication with the hypobaric interior of the vessel 40, a pressure gradient is created across the filter media 20 as was previously described. This draws the liquid specimen 39 from the collection receptacle 10 through the filter media 20 and ultimately into the disposal vessel 40 (see FIG. 3). While other means can be used to generate a flow of the liquid from the collection receptacle, through the filter container and into the hypobaric chamber, the use of a hypobaric vessel such as a Vacutainer™ type tube has a distinct advantage in that it provides a consistent measured initial force for drawing in a defined volume of fluid, providing consistent and predictable collection results.

The filter captures and collects the cellular component of the specimen as it passes therethrough to define a cell sample 42 (see FIG. 4). The discharged portion of the specimen is collected in the vessel 40 for suitable disposal.

One of the advantages of the present invention is the ability to perform multiple analyses on the same sample. The designs of the following two embodiments are intended to augment this advantage by avoiding or minimizing of physical manipulation or segmentation of the filter material itself. One embodiment facilitates the punching out of discs from the filter while it is still enclosed in the housing; while another embodiment permits the collection on multiple separate filters which can then be handled separately without any physical separation or segmentation process.

A second embodiment of the collection apparatus is shown in FIG. 9, the filter container being shown in greater detail in FIGS. 6–8. In this embodiment the disposal vessel 40 is a hypobaric chamber essentially the same as in the previous embodiment. The collection receptacle 80 is funnel shaped and is particularly well suited for collecting urine specimens and the like. It includes a discharge port 14 adapted to sealingly mate with the inlet port 24 of the filter container of this embodiment. It should be understood that the various collection receptacles, the disposal vessels and the filter containers are esentially interchangeable between embodiments. One has only to ensure that the discharge and inlet ports can sealingly engage, and that the outlet port and hypobaric chamber can be selectively put into sealable communication, such as by means of a hypodermic needle 30 (see FIG. 9) which may then be inserted in a typical hypobaric device for drawing the fluid through the discharge port of the receptacle 80 and into the filter container 58, in the manner previously described.

With reference to the filter container 58 shown in FIG. 6–8, this embodiment of the filter container comprises a pair of mated sections 60 and 62, adapted for sealable engagement in use. The upper section 60 (as shown) includes a filter support plate 70 for supporting an annular filter 72 (see FIG. 8). The filter support 70 may preferably be detachable from the upper housing section 60 for ease in inserting a filter medium. The annular filter 72 includes a central aperture 74 which is adapted to be received in the raised boss 71 provided on the support plate 70 for properly seating the filter 72 relative to the support surface. The support plate 70 includes a plurality of apertures 76 through which the liquid specimen can pass as it is drawn through the filter container 58.

The lower container section 62 includes a disc shaped plate or support 64 which abuts against the support 70 of upper section 60 when the container 58 is assembled as shown in FIG. 6. The plate 60 includes a plurality of apertures 66 aligned with apertures 76 in the support surface 70. In a variation (shown in FIG. 10) the support plate 70 may be integrally formed or fused with the support plate 60. A porous plug 68 may be placed in the apertures 66, 76 to further direct flow therethrough. This assures adequate contact between the filter media and the liquid specimen for providing a sufficient capture of the cellular sample on the filter and can also serve to channel and concentrate the collection of cells in discrete areas 77 on the filter 72 surrounding the positions of the apertures 76. This discrete zone collection is illustrated in FIG. 8, which may be compared with FIG. 4, wherein the cells are collected "en masse" in a central area 42.

Discrete zones of collected cells provides two advantages. First, the zones are easier to divide or section into aliquots for performing a plurality of analyses. Second, the distribution of specimen flow to discrete areas of the filter 72 may minimize and delay membrane fouling. This distribution or channeling may be accomplished by channels or apertures below the filter media (e.g. apertures 76), or by passages or "manifolds" leading up to the filter media (e.g. manifold 106 described below in connection with FIGS. 11–14).

After collection of the cell sample 42, the halves 60, 62 of the filter container 58 may be separated and the filter 72 removed. It may be dried, sectioned, transported and/or analyzed by any desired means, as with the other filter 20.

Figure 11:
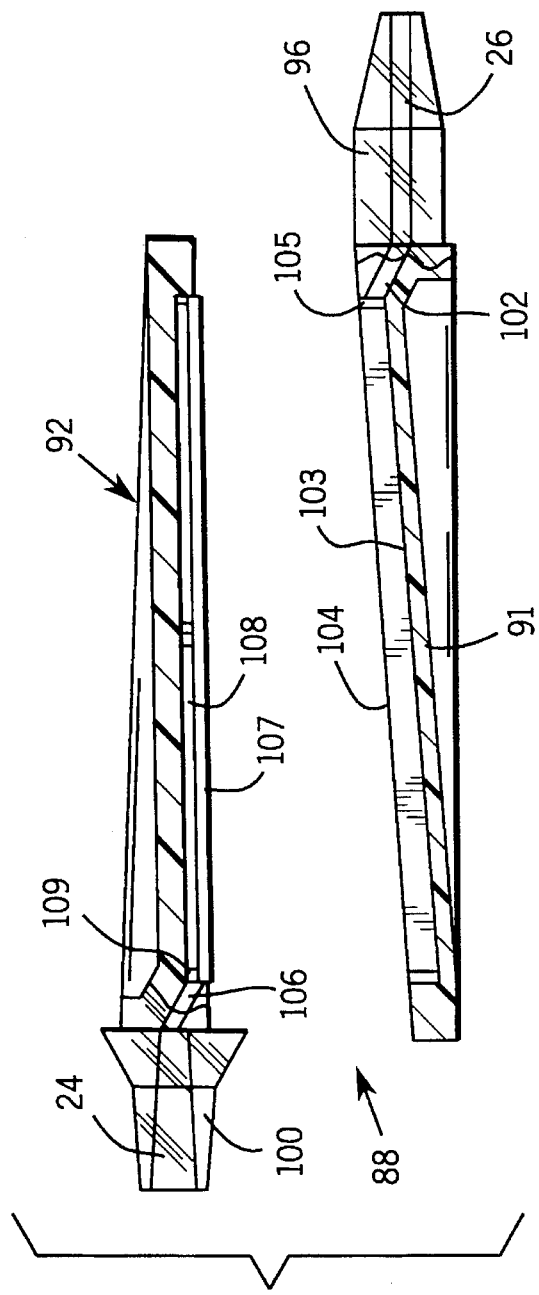
FIG. 11 illustrates an alternative embodiment of the filter container as shown in the kit assembly of FIG. 5, with the filter container disassembled to provide access to the filter media.
Figure 14:
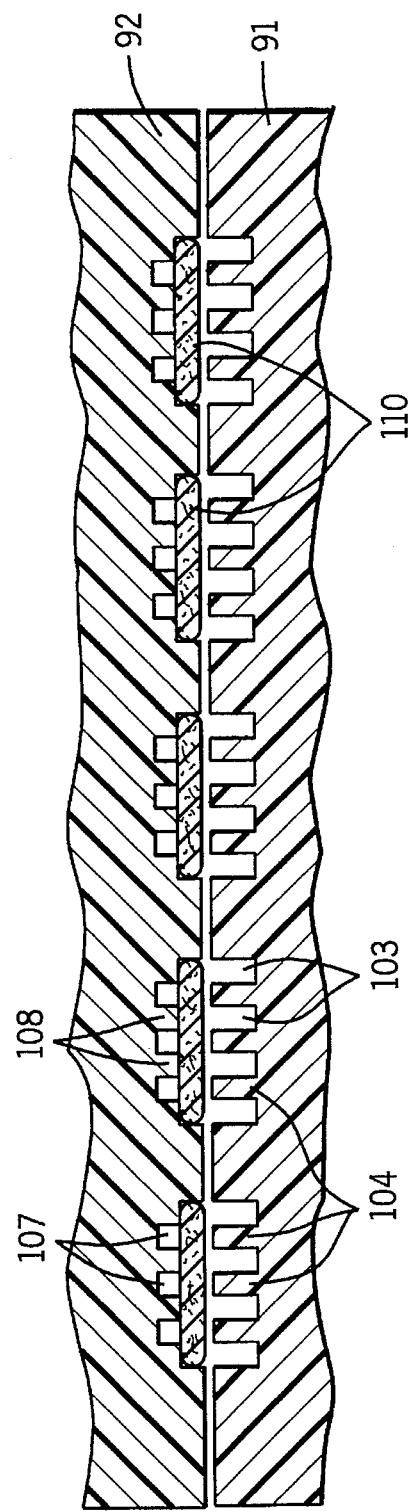
FIG. 14 is an enlarged cross section taken generally along line 14—14 of FIG. 11, but with the top and bottom halves in mated relationship.

A variant method for removing cell samples 42 from the filter container 58 is shown in FIG. 10. In this variation the filter container 58 includes a plurality of openings 84 around the perimeter of the upper wall 83 of the filter housing member 60. The openings 84 are in axial alignment with the apertures 66, 76 and the associated zones 77, and are initially closed with a removable membrane or seal 81. After the cell sample 42 is collected in each of the various zones 77 on the filter, the bottom member 62 of the container 58 is removed. A suitable receptacle such as vial 85 is then placed in communication with a selected zone 77 as shown in FIG. 10. Typically, the vial 85 will include an open mouth have an outer lip or rim 87 adapted to be inserted into or connected with a respective aperture 76. A tool such as punch 86 includes a tip 89 which is adapted to punch the associated cell sample zone 77 out of the disc and into the vial 85 where it can be stored for analysis. Prior to using the punch 86, the seal 81 may be peeled away from openings 84 in the upper housing member 60 or the punch may be adapted to puncture the seal 81 as well. This alternative method for removing cell samples does not require that the entire filter be removable from the housing A third filter container embodiment is shown in FIGS. 11–14. As there shown, a manifold filter container 88 comprises a pair of substantially rectangular sections members or halves 91 and 92. Each of these sections can be formed from a unitary mold with integral flow paths in the manner well-known to those skilled in the art. As shown in FIGS. 11 and 13, an inlet port 24 is provided in the nipple 100 extending outwardly from the right end of the lower section 92. An outlet port 26 is provided in the outlet nipple 96 extending from the left end of upper section 91 (see FIGS. 11 and 12). Longitudinal grooves 103 are molded into the upper section 91 for defining the longitudinal lands or ribs 104. Similar longitudinal grooves 107 are molded into lower section 92 for defining the longitudinal lands or ribs 108. An integral through channel 102 is provided in the nipple 96 and communicates the upper filter grooves 103 with outlet port 26, via manifold 105. Likewise, an integral through channel 106 is provided in inlet nipple 100 and communicates the lower filter grooves 107 with the inlet port 24, via manifold 109. The ribs 104 and 108 are preferably staggered (see FIG. 14) to create diagonal flow-paths through the filter media element 110 to maximize the area to which the specimen is exposed as it is drawn through the filter container, to maximize the cell yield in the captured cell sample. In use, the filter media element(s) 110 is placed in the longitudinal grooves on the ribs 108 and is sandwiched between the upper and lower sections when assembled as shown in FIG. 14. The inlet nipple 96 is adapted to be secured to the discharge port of a suitable collection receptacle and the outlet nipple 100 is adapted to be secured to a suitable disposal vessel in the manner previously described.

In use, a filter media is placed in each groove and the halves are sealed together. Locking tabs or clamps (not shown) may be provided for sealingly engaging the container halves. A collection receptable is sealingly engaged at the inlet end. When a pressure differential is created between the inlet port 24 and the outlet port 26 the liquid in the collection receptacle flows through the integral channels defined by the ribs and grooves, as shown in FIG. 14 to capture the cell samples.

One advantage of this embodiment is that more cells or particulates can be filtered as the filter element 110 near the inlet becomes clogged by allowing the fluid specimen to flow through the grooves 103 until it reaches a less clogged portion of the filter media. It will be readily understood by those who are skilled in the art that the particular configuration of the ribs and grooves is a matter of design choice and is largely dictated by the size of the cellular structure being captured in the cell sample.

As is particularly shown in FIG. 5, the collection apparatus of the invention can be assembled in kit form for ready use in a clinical environment. The kit typically includes a collection receptacle 10, one or more filter containers 58, 88, a hypobaric vessel 40 with a seal such as cap 38, and means for applying the pressure differential of vessel 40 to the outlet port 26 of the filter container. The means for applying pressure may be the needle assembly 30 which is adapted to be attached to the discharge end 26 of the respective filter containers and to puncute the seal 38 of the vessel 40. The component filter container 58, 88, collector receptacle 10, needle assembly 30 and hypobaric chamber 40 are all described in detail above.

Part III: Examples

Examples were run under laboratory conditions and demonstrate the functionality of the invention as disclosed herein. The following abbreviations are used consistently with respect to the examples:

| | |
|---|---|
| BSA: | Bovine serum albiumin |
| CF: | Cystic fibrosis |
| CFTR: | Cystic fibrosis transmembrane regulator |
| EPPS: | a buffer comprising N-(2-hydroxyethyl)piperazine-N'-(3-propane sulfonic acid) |
| oligos: | Oligonucleotides, generally oligo-2-deoxyribonucleotides |
| NAD: | Nicotine adenine dinucleotide |
| TRIS: | a buffer comprising tris(hydroxymethyl)aminomethane |
| units: | a measure of the concentration of enzyme. Units for polymerase are as expressed by the manufacturer; units for ligase are defined such that 1 mg of 95% purified DNA ligase has a specific activity of about $1 \times 10^8$ units. |

Example 1: General Cell Collection Device

Filtration-Collection devices according to the present invention were assembled as follows: Millipore (Millipore Corporation, Bedford, Mass.) AP25, 1 inch diameter glass fiber pre-filters were assembled into 25 mm Swinnex Disc Filter Holders (Millipore, Bedford, Mass.). These were then attached to a 20 or 50 ml standard syringe barrel via the Luer entry port. Hollow bore hypodermic needles, 16 gauge, 1 inch long were attached to the Luer fitting at the exit port. Samples are collected (see examples below for details) in the syringe barrel which acts as a convenient funnel and the filtration is achieved by inserting the needle through the rubber stopper of a Vacutainer™ tube (Becton Dickinson, Rutherford, N.J.) and performing the filtration. When the filtration process terminates, the excess liquid sample is discarded, the device dissembled and the filter processed as in following examples.

Example 2: Specimen Collection:

A. Water Rinse: Each individual took 10 ml of drinking water and rinsed it a few times in their mouths to constitute the liquid specimen, and then expectorated the specimen into the opening of a collection receptacle. A Vacutainer™ vessel was connected to apply a pressure gradient and the cell sample was collected on the filters as described above. After collection, the filters were removed from the collection device and air dried on a lab bench. Dried filters were either processed or stored in a plastic bag at room temperature for up to 47 days until processing.

B. Antiseptic Mouthwash Rinse: Samples were collected as in part A, except the individuals used 10 ml of commercially available antiseptic mouthwash (Scope®, Proctor & Gamble, Cincinnati, Ohio) to constitute the liquid specimen. The AP40 filters disintegrated after collection and sample processing (see below).

Example 3: Processing of Collected Cell Samples:

A. Some of the collected filters were placed in a 1.7 ml Microcentrifuge tube and 0.5 ml of sterile HPLC water was added. The sample tube was then incubated in boiling water for 20 min. and then cooled to room temperature. The liquid was removed to a new tube after a quick spin.

B. Other samples were collected as above, followed by an alternative KOH extraction. These sample filters were processed with 0.5 ml of 50 mM KOH. After incubation in boiling water for 20 min. 100 μL of 0.1 M Tris-HCl, pH 7.5, was added to neutralize the solution. The solution was then centrifuged for 20 min at 14,000 rpm and the supernatant was transferred to a new tube.

Example 4: LCR® Amplification and Detection of CFTR gene

A. Amplification: LCR® amplification was performed using the so-called "double-gap" strategy as described by Backman, et al. in European Patent Application 0 439 182 (1991). Four probes (SEQ ID NOS. 1, 2, 3 and 4) were synthesized and labeled with biotin or fluorescein haptens as shown below using standard techniques known in the art.

Calif.), and 3400 units of *Thermus thermophilus* DNA ligase. 10 μL of processed cell sample from Example 3A was used for each amplification. Human placental DNA (50 ng) was used as control to monitor the amplification process. The LCR® process itself occurred in a model 480 Thermal Cycler (Perkin-Elmer, Norwalk, Conn.) using a denature profile of 95° C. for 3 minutes followed by a cycling profile of 85° C. for 30 sec and 57° C. for 60 sec.

B. *Detection by Immunochromatography*: Antisera to adamantane, fluorescein, and biotin were raised in rabbits against adamantane-BSA, fluorescein-BSA or biotin-BSA. These antisera were purified by passage through protein A Sepharose® or protein G Sepharose® (Pharmacia, Piscataway, N.J.) and diluted in 0.1M TRIS pH 7.8, 0.9% NaCl, 0.1% BSA, 1% sucrose, and a trace of phenol red. Portions (0.2 μL) of these diluted anti-adamantane and anti-fluorescein antisera were jetted onto 7.3×40 mm strips of nitrocellulose (AE98, 5 μm, Schleicher and Schuell, Dassel, Germany).

Anti-biotin antiserum was conjugated to polystyrene uniformly-dyed blue latex particles (Bangs Laboratories, Carmel, Ind.). Particles (380 nm diameter) were diluted 1.25 in water to give 1 ml at 0.4% solids and 10 μL of anti-biotin at 1 mg/ml was added. The suspension was mixed on a vortex mixer for 45 seconds, and 5 μL of 5% casein in 0.1M TRIS pH 7.8 was added.

For detection, 21 μL of the anti-biotin conjugate (blue latex) was diluted with 16 μL buffer (0.1M TRIS pH 7.8 0.9% NaCl, 3% alkali-treated casein), and mixed with 5 μL of LCR® amplification product. A nitrocellulose strip containing anti-fluorescein or anti-adamantane, or both, was introduced to the conjugate suspension, and chromatography was allowed to proceed for five minutes, substantially as described in published application EP 0 357 011 A2. The strip was dried and is shown in FIG. 17. The presence of a colored spot at the locus of anti-fluorescein application indicated the presence of a specific LCR® product.

FIG. 17 shows sample strips processed from different individuals at different times following collection on filters as follows: Strip C. is purified placental DNA. Strips 1–5 are samples from 5 different individuals processed from filters 47 days after collection (strip 1), 45 days after collection (strip 2), and one day after collection (3 individuals, strips 3, 4 and 5); and strip B is a blank control, with no DNA added.

Example 5: LCR® Amplification and Detection of β globin gene

A. *Amplification*: LCR® amplification was performed using the so-called "double-gap" strategy as described by Backman, et al. in European Patent Application 0 439 182

|  |  | SEQ. ID No. |
|---|---|---|
| Probes #1. | 5'-fluorescein-GGCACCATTAAAGAAAATATCA-3' | 1 |
| Probes #2. | 5'-p-GATATTTTCTTTAATGGTGCC-3' | 2 |
| Probes #3. | 5'-p-GGTGTTTCCTATGATGAATATAG-biotin-3' | 3 |
| Probes #4. | 5'-biotin-CTATATTCATCATAGGAAACACCAAAGA-3' | 4 |

The alignment of these probes with exon 10 of the CFTR gene (SEQ ID No. 5) is shown in FIG. 15. The target is region 1612–1690 as numbered by Zielenski et al., Genomics 10, 214–228 (1991).

LCR was carried out for 40 cycles with each of the four probes (SEQ ID NOS. 1, 2, 3 and 4) in a total volume of 100 μL with the following final concentrations: 50 mM EPPS pH 7.8, 20 mM potassium (added as KOH to adjust the pH of the buffer and as KCl to achieve 20 mM K+), 30 mM MgCl$_2$, 100 μM NAD, 10 μM nucleoside triphosphates dCTP and dTTP, 100 μM of each of the 4 probes, 3 units of DNA polymerase (Amplitaq®, Perkin-Elmer/Cetus, Emeryville, (1991). Four probes (SEQ ID NOS. 6, 7, 8 and 9) were synthesized and labeled with biotin or adamantane haptens as shown below using standard techniques known in the art. The alignment of these probes on the β- globin gene (SEQ ID No. 10) is shown in FIG. 16.

|  | | SEQ ID No. |
|---|---|---|
| Probe 1. | 5'adamantane-CCGAGGGCCTCACCACCAACTTCA-3' | 6 |
| Probe 2. | 5'-p-GAAGTTGGTGGTGAGGCCCTGGG-3' | 7 |
| Probe 3. | 5'-p-CCACGTTCACCTTGCCCCACAGG-biotin-3' | 8 |
| Probe 4. | 5'-biotin-CCTGTGGGGCAAGGTGAACGTGGA-3' | 9 |

LCR® amplification was carried out as in Example 4A except that only dTTP is needed to fill the gap in these probes; and 10 µL cell samples processed with both water and KOH extractions were used (see Examples 3A and 3B).

B. *Detection by Immunochromatography*: Immunochromatographic strips are prepared as in Example 4B. Detection of amplified products was performed as described above except the following conjugate was used.

Anti-biotin antiserum was conjugated to polystyrene uniformly-dyed blue latex particles (Molecular Probes, Inc. Eugene, Oreg.). Particles (306 nm diameter) were diluted in 1/40 in water to give 5 ml at 0.05% solids. and 50 µL of anti-biotin at 1 mg/ml was added. The suspension was mixed for 5 min. 50 µL of 5% casein in 0.1M TRIS pH 7.8 was then added and mixed for 15 min. The solution was transferred to 1.7 ml microcentrifuge and centrifuged for 10 min 16 10,000 rpm. The supernatant was then removed. Pellet from original 1 ml solution was resuspended with 980 ml of HPLC grade water and all five ml were combined.

Data from this example is shown in FIG. 18, wherein the following annotations are used: Strip C. is purified placental DNA (50 ng); Strips 1 to 3 are from filters processed by water extraction per example 3A; Strips 4 and 5 are from filters processed by KOH extraction per example 3B with the addition of spiked-in pure placental DNA (50 ng).

From these experiments and others (data not shown) it has been observed that conventional KOH extraction can be used for blunt LCR, but is not suitable for Gap LCR (note the absence of signal in strips 4 and 5 of FIG. 18. Apparently, the KOH extraction protocol causes inhibitors of Amplitaq® DNA polymerase to be co-extracted. In the case of Gap LCR, the water extraction alternative protocol is preferred.

It is also observed that tap water appears to be better than Scope® mouthwash for obtaining viable cells. Experience with Scope® shows that the filter disintegrated completely, perhaps due to the alcohol content of this commercial product.

While certain features and embodiments have been described in detail herein, it will be readily understood that the invention may include other modifications and enhancements. The invention for which protection is sought is defined by the following claims.

What is claimed is:

1. A method for collecting on a filter media cells from a liquid specimen having a cellular component, the method comprising the steps of:

depositing a liquid specimen suspected of having a cellular component into an open end of a collection receptacle having a discharge port;

placing the discharge port in fluid communication with a filter media by means of a sealed passage therebetween, the filter media having a pore size sufficiently small to retain desired suspected cells from the liquid specimen,. wherein the filter media is housed between an inlet port and an outlet port of a filter container, the inlet port being adapted for sealably engaging the discharge port; and applying a pressure differential across the filter media and extending to the liquid specimen by means of the sealed passage to force the liquid specimen through the discharge port of the collection receptacle and through the filter media, wherein said differential pressure is applied by puncturing a penetrable closure element of a closed hypobaric chamber with said outlet port in order to put said outlet port and closed hypobaric chamber in sealed fluid communication, thereby placing the filter container under a relative vacuum and capturing on the filter media a sample of any cellular component of the liquid specimen.

2. The method of claim 1, including the further steps of removing at least some of the filter media from the filter container and drying the sample collected on the filter media.

3. The method of claim 2, comprising a step of segmenting the filter media and captured sample into discrete sections for separate analysis.

4. The method of claim 3, wherein the filter container includes means for distributing the liquid specimen to discrete areas of the filter media.

5. The method of claim 2, including one or more further steps selected from storing or transporting a sample dried on said filter media.

6. The method of claim 1, including a further step of processing the sample for analysis of the presence or amount of a selected constituent.

7. The method of claim 6, wherein the selected constituent is a segment of nucleic acid.

8. The method of claim 7, wherein the nucleic acid segment is amplified prior to said analysis.

9. The method of claim 1, wherein said liquid specimen is a high-volume specimen.

10. The method of claim 9, wherein said liquid specimen is a mouthwash specimen.

11. The method of claim 1, wherein said puncturing includes mounting a hollow bore needle to said outlet port and puncturing the penetrable closure element with said needle.

12. A cell collection apparatus for collecting, archiving and/or transporting a cell sample generated from a liquid specimen, comprising:

a collection receptacle having an open end for receiving a liquid specimen and a discharge port through which said liquid specimen can leave the collection receptacle;

a filter container having an inlet port adapted for sealably engaging the discharge port of said collection receptacle, an outlet port through which said liquid specimen can leave the filter container and a filter media supported in the filter container between said inlet and outlet ports, whereby the liquid specimen entering said filter container via the inlet port passes through said filter media before leaving via said outlet port, said filter media being adapted for receiving and capturing a cellular component of the liquid specimen for defining a cell sample for analysis and said outlet port being adapted for sealably puncturing a rupturable seal; and a hypobaric vessel having a rupturable seal, whereby puncturing said rupturable seal with said outlet port places them in sealed communication such that a relative vacuum is applied to the outlet port thereby drawing the liquid specimen through the filter media.

13. The cell collection apparatus of claim 12, wherein said hypobaric vessel serves as a discharge vessel for receiving the liquid specimen passing through the filter media and the outlet port of the filter container.

14. The cell collection apparatus of claim 12, wherein the filter media is a discrete element, all or part of which is removable from said filter container.

15. The cell collection apparatus of claim 12 wherein the filter container comprises a pair of mated members, the first member including a filter media support adapted for retaining and seating the filter media, and the second member adapted to be placed in mated assembly with the first member to form an assembled container for releasably housing the filter media.

16. The cell collection apparatus of claim 12, further comprising a filter support means for supporting the filter media.

17. The cell collection apparatus of claim 16, wherein said filter support means comprises a plate having a plurality of apertures for localizing collected cells in discrete areas corresponding to said apertures.

18. The cell collection apparatus of claim 17, wherein said filter container defines holes in registration with the apertures in said plate, said holes and apertures being adapted for receiving a punch to punch out and remove sections of the cell sample from the filter container.

19. The cell collection apparatus of claim 12, further comprising channeling means for distributing the liquid specimen to discrete areas of the filter media or to distinct filters.

20. The apparatus of claim 12, further including a hollow bore needle adapted to be secured to said outlet port for sealably puncturing the rupturable seal of said hypobaric vessel.

21. A cell sample collection kit for collecting and obtaining for analysis a cell sample from a liquid specimen, the kit comprising:

a filter container having an inlet port and an outlet port;

a filter media removably housed in the filter container between the inlet and outlet ports;

a collection receptacle having an open end for receiving a liquid specimen and a discharge port adapted to be selectively mounted in communication with the inlet port of the filter container;

a hypobaric chamber adapted to be placed in communication with the outlet port of the filter container for generating a pressure differential across the filter media for drawing the liquid specimen from the collection receptacle and through the filter media for capturing a cellular component of the liquid specimen on the filter media; and a hollow bore needle adapted to be mounted on the outlet port of the filter container, the needle bore being in communication with the outlet port of the filter container when mounted thereon, the hypobaric chamber including a closure adapted to be punctured by the tip of the needle for drawing the liquid specimen from the collection receptacle into the filter container and through the filter media for discharge through the outlet port into the hypobaric chamber.

22. The kit of claim 21, wherein the filter media is supported within the filter container by a supporting ridge or plate.

23. The kit of claim 21, wherein the filter container further includes channel means for distributing the liquid sample to discrete areas of said filter media.

24. The kit of claim 21, wherein said filter media is made of a material selected from the group consisting of glass fiber, paper and cellulose esters.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:1:

GGCACCATTA AAGAAAATAT CA        22

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GATATTTTCT TAATGGTGC C        21

( 2 ) INFORMATION FOR SEQ ID NO:3:

( i ) SEQUENCE CHARACTERISTICS:

( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

GGTGTTTCCT ATGATGAATA TAG 23

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

CTATATTCAT CATAGGAAAC ACCAAAGA 28

( 2 ) INFORMATION FOR SEQ ID NO:5:

( i ) SEQUENCE CHARACTERISTICS:
        ( A ) LENGTH: 68 base pairs
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO:5:

TATGCCTGGC ACCATTAAAG AAAATATCAT CTTTGGTGTT TCCTATGATG AATATAGATA 60

CAGAAGCG 68

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:6:

CCGAGGGCCT CACCACCAAC TTCA 24

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:7:

GAAGTTGGTG GTGAGGCCCT GGG 23

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single -continued ( D ) TOPOLOGY: linear ( i i ) MOLECULE TYPE: DNA (synthetic)

( x i ) SEQUENCE DESCRIPTION: SEQ ID NO:8:

CCACGTTCAC CTTGCCCCAC AGG        23

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:9:

CCTGTGGGGC AAGGTGAACG TGGA        24

( 2 ) INFORMATION FOR SEQ ID NO:10:

( i ) SEQUENCE CHARACTERISTICS:
        ( A ) LENGTH: 47 base pairs
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO:10:

CCAGGGCCTC ACCACCAACT TCATCCACGT TCACCTTGCC CCACAGG        47